United States Patent [19]

Tankovich et al.

[11] Patent Number: 5,423,803

[45] Date of Patent: Jun. 13, 1995

[54] SKIN SURFACE PEELING PROCESS USING LASER

[75] Inventors: Nikolai I. Tankovich, San Diego; Kenneth Y. Tang, Alpine; Allen M. Hunter, San Diego, all of Calif.

[73] Assignee: ThermoTrex Corporation, San Diego, Calif.

[21] Appl. No.: 257,021

[22] Filed: Jun. 8, 1994

Related U.S. Application Data

[63] Continuation-in-part of Ser. No. 5,810, Jan. 19, 1993, which is a continuation-in-part of Ser. No. 783,789, Oct. 29, 1991, Pat. No. 5,226,907.

[51] Int. Cl.$^6$ ............................................. A61N 5/06
[52] U.S. Cl. ........................................ 606/9; 606/131
[58] Field of Search ............................ 606/4, 9, 131

[56] References Cited

FOREIGN PATENT DOCUMENTS 0166123  5/1980  Japan ..................................... 606/9

OTHER PUBLICATIONS

Kaufmann et al, Cutting and Skin-Ablative Properties of Pulsed Mid Infared Laser Surgery J Dermatol Surg Oncol 1994; 20:112–118.

Coleman, Cosmetic Surgery–J. Dermatol Surg Oncol 1994; 20:332–335.

Primary Examiner—Stephen C. Pellegrino
Assistant Examiner—Glenn Dawson
Attorney, Agent, or Firm—John R. Ross

[57] ABSTRACT

A process for the removal of superficial epidermal skin cells in the human skin. A contaminant having a high absorption at at least one wavelength of light is topically applied to the surface of the skin. Some of the contaminant is forced to infiltrate into spaces between the superficial epidermal cells. The skin section is illuminated with short laser pulses at the above wavelength, with at least one of the pulses having sufficient energy to cause some of the particles to explode tearing off the superficial epidermal skin cells. In a preferred embodiment, the contaminant includes 1 micron graphite particles and the laser used is a Nd:YAG laser.

14 Claims, 13 Drawing Sheets

1

SKIN SURFACE PEELING PROCESS USING LASER

This invention is a continuation in part of Ser. No. 08/005,810 filed Jan. 19, 1993, now pending which was a continuation in part of Ser. No. 07/783,789 filed Oct. 29, 1991, now U.S. Pat. No. 5,226,907 issued Jul. 13, 1993. This inventions relates to processes for removal of the surface layer of human skin and in particular to such processes which utilize lasers.

BACKGROUND OF THE INVENTION

The epidermis of the human skin comprises several distinct layers of skin tissue. These layers of tissue are shown in block diagram form in FIG. 1. The deepest layer is the stratum basale layer which consists of columnar cells. The next layer up is the stratum spinosum composed of polyhedral cells.

Cells pushed up from the stratum spinosum are flattened and synthesize keratohyalin granules to form the stratum granulosum layer. As these cells move outward they loose their nuclei and the keratohyalin granules fuse and mingle with tonofibrils. This forms a clear layer called the stratum lucidum. The cells of the stratum lucidum are closely packed.

As the cells move up from the stratum lucidum they become compressed into many layers of opaque squamas. These cells are all flattened remnants of cells which have become completely filled with keratin and have lost all other internal structure, including nuclei. These squamas constitute the outer layer of the epidermis, the stratum corneum. At the bottom of the stratum corneum the cells are closely compacted and adhere to one another strongly, but higher in the stratum they become loosely packed and eventually flake away at the surface. For example, in the cheek skin of a 50 year old face the outer layer of the corneum stratum typically consists of about 15 layers and the layers flake away at the rate of about one or two layers per month. So we naturally get a completely new stratum corneum about twice per year.

It is well known that the removal of a few surface layers of a person's skin will generally result in younger looking skin. Many techniques have been tried to produce this effect. A mild sunburn will cause slight blistering of the skin after which an outside layer of the skin peels off. This generally leaves a younger looking skin surface. Similar results can be obtained by abrasion processes such as actually scraping away the surface layer with an abrasive material such as fine sand paper.

Recent attempts have been made to utilize laser beams to "cook" the surface layer of skin. This cooking causes the skin to blister after which the surface layers can be scraped away. Also, people have been experimenting with lasers which vaporize the outside surface. These prior art processes present some beneficial results but also provide potential risk to the patient. The slight sunburn presents a risk of underlying long term damage to the skin. Abrasion processes often result in bleeding and pain and sometimes infection, scabbing, and slight scarring. Laser treatments can result in pain and undesired burning, and if not applied properly can result in bleeding and scarring.

SUMMARY OF THE INVENTION

The present invention provides a process for the removal of superficial epidermal skin cells in the human skin. A contaminant having a high absorption at at least one wavelength of light is topically applied to the surface of the skin. Some of the contaminant is forced to infiltrate into spaces between the superficial epidermal cells. The skin section is illuminated with short laser pulses at the above wavelength, with at least one of the pulses having sufficient energy to cause some of the particles of the contaminant to explode tearing off the superficial epidermal skin cells. In a preferred embodiment we use 1 micron graphite particles and a Nd:YAG laser.

BRIEF DESCRIPTION OF THE DRAWINGS

Preferred embodiments of the present invention can be described by reference to the drawings.

DETAILED DESCRIPTION OF THE PREFERRED EMBODIMENTS

First Preferred Embodiment—Nd:YAG

Outer Layers of the Epidermis

Figure 1:
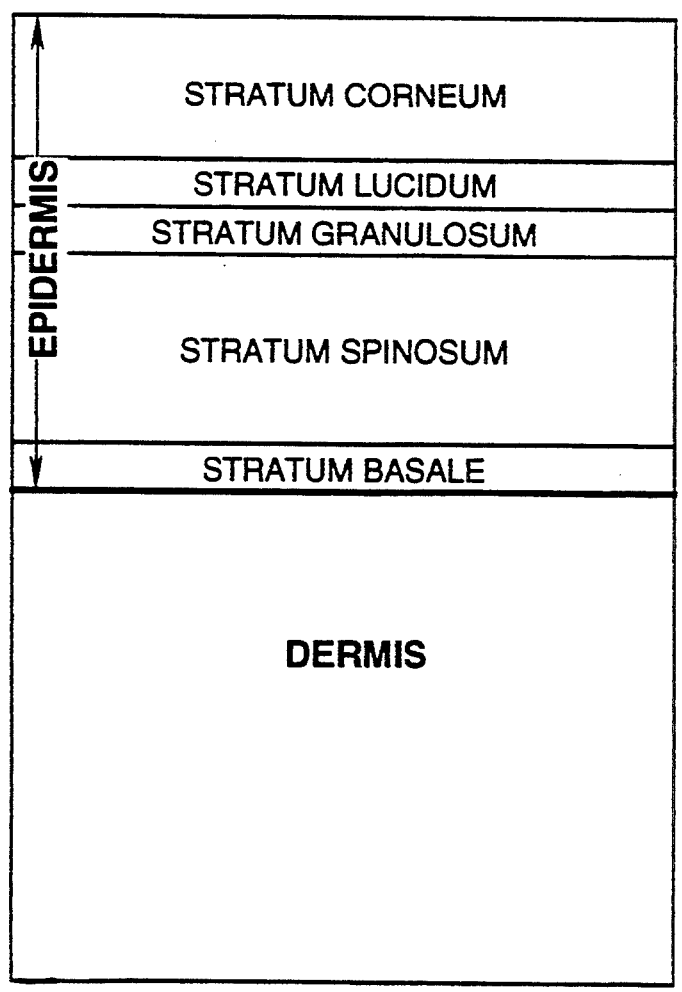
FIG. 1 is a cross-sectional representation of human skin.
Figure 2:
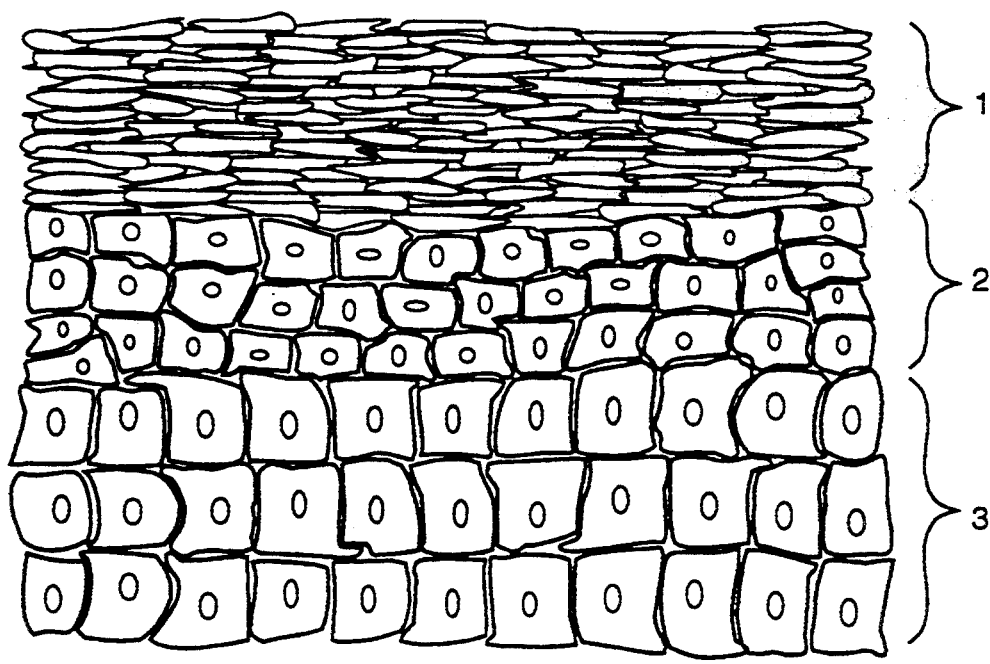
FIG. 2 show 3 layers of the epidermis.

A first preferred embodiment of the present invention can be described by reference to FIGS. 2 through 10. FIG. 2 shows a typical cross section of a section of the outer portion (the top three strata) of the human epidermis such as that in the skin of a 50 year old female's cheek. Shown is a representation of a 15-cell thick stratum corneum 1, and a 3-cell thick stratum lucidum 2, and a 3-cell thick stratum granulosum. The total thickness shown is about 100 microns (0.10 mm).

Individual cells of the stratum corneum have dimensions of about 10 to 15 microns long, about 5 microns wide and up to 2 microns thick. The cells of the upper layers are loosely stuck together. Spaces between the cells range from zero distance to about 1 or 2 microns.

Application of Carbon Solution

Figure 3:
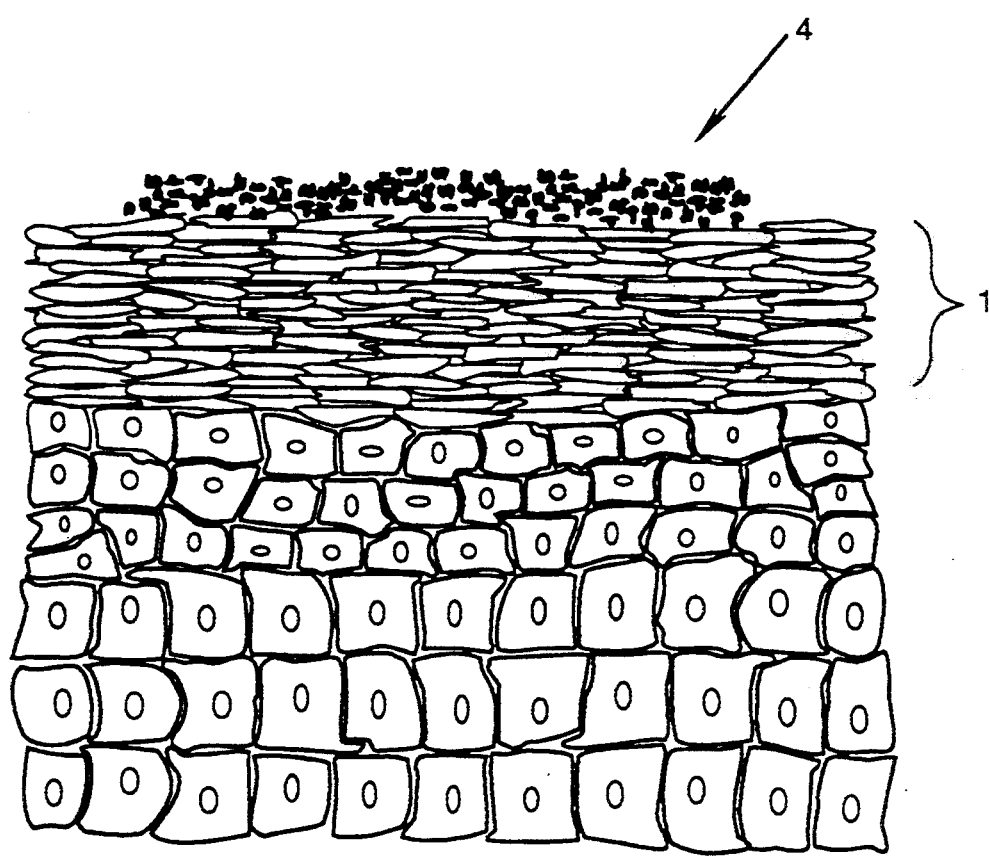
FIG. 3 shows a topical application of a carbon solution.
Figure 4:
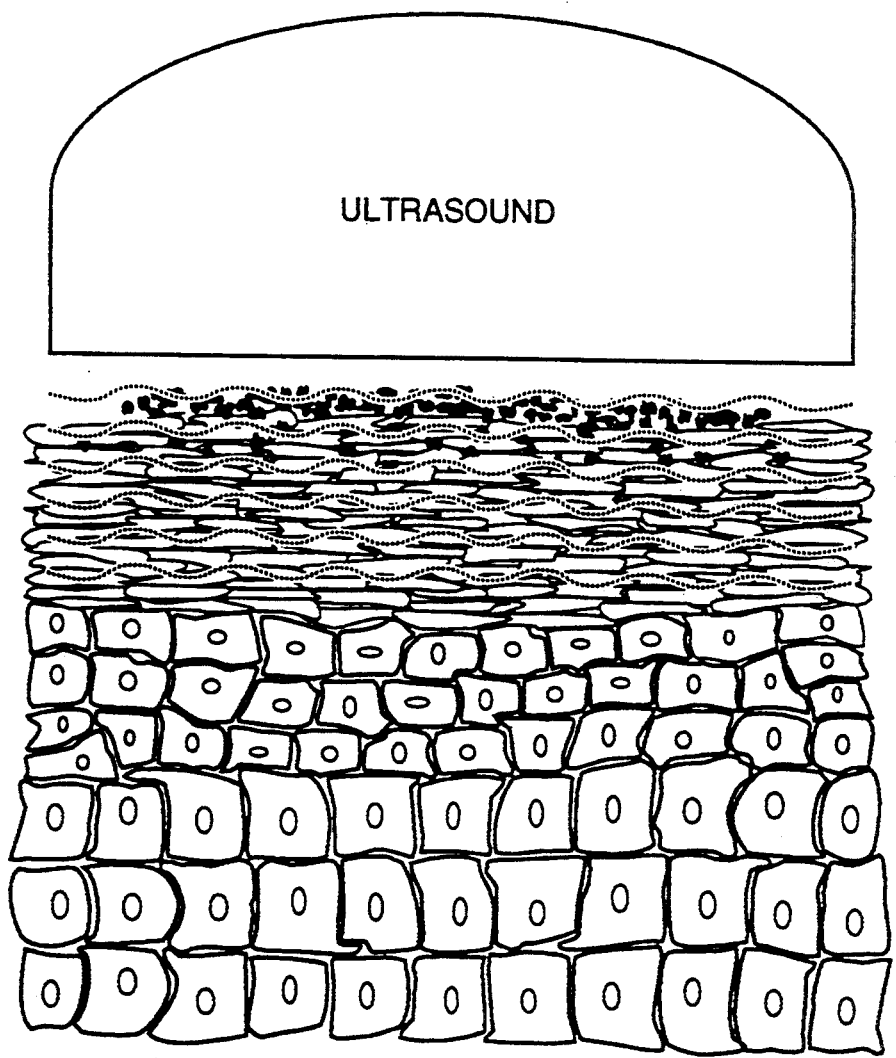
FIG. 4 shows ultrasound device in operation on the solution.

The first step of this preferred embodiment is to topically apply a layer of carbon solution to the skin surface as shown in FIG. 3. The solution is comprised of 1 micron graphite powder in baby oil. The graphite-oil ratio is 20 percent graphite suspended in 80 percent oil by weight. The next step FIG. 4, is to force some of the carbon particles down below the surface of the stratum corneum. We prefer to do this with an ultrasound unit operating at 0.2 watts per $cm^2$ and 10 MHz.

Figure 5:
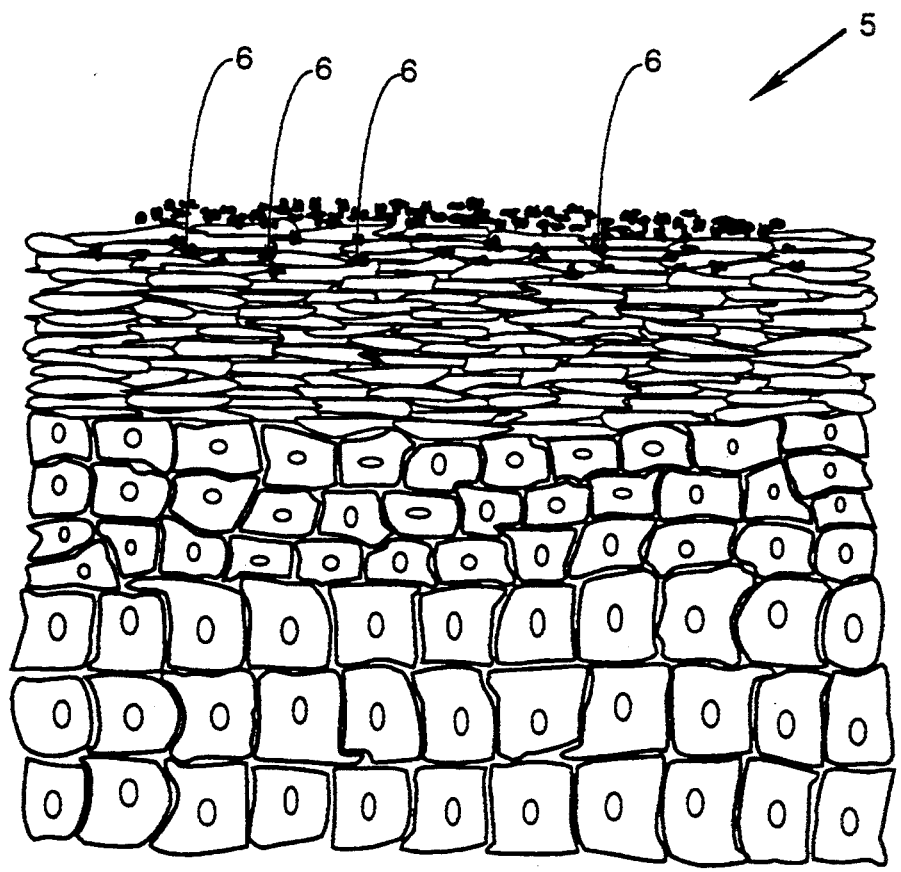
FIG. 5 shows the result of the above operation.

We use a Hewlett Packard Model 3325A pulse generator and a Parametrics transducer model A5525. We have found that approximately 5 minutes of ultra sound treatments at this frequency will force a significant number of carbon particles down through several layers of the stratum corneum. The result of the ultrasound treatment is shown in FIG. 5. This distribution of carbon particles has been demonstrated on pig skin. Microscopic examination of biopsy samples from the pig skin show the distribution depicted in FIG. 5. As shown in FIG. 5, two layers of graphite particles are left on the surface and a portion of the particles 6 are distributed below the surface.

Pulse Irradiation

The next step is to irradiate the skin surface with Nd:YAG laser pulses of about 3 J/cm$^2$ at a wavelength of 1.06 $\mu$m. Pulse frequency is about 5 Hz but we scan the beam so that each location is subjected to pulses at a frequency of about 1 Hz. Graphite is very absorptive of laser energy at the 1.06 $\mu$m wavelength. The latent heat of vaporization is about $10^4$ J/cm$^3$ for cold solid graphite. Thus, to vaporize a 1 micron cube ($10^{-12}$ cm$^3$) would require approximately $10^{-8}$ J. The energy falling on the surface of the 1 micron particle ($1 \times 10^{-8}$ cm$^2$) in a 3 J/cm$^2$ pulse is $3 \times 10^{-8}$ J, about three times the energy needed to vaporize the particle. The energy is deposited in a few nanoseconds so there is no time for the heat to diffuse therefore its explodes violently upon being illuminated by the pulse. The effect of one pulse is to vaporize some of the graphite (especially smaller particles) and to break larger graphite particles into smaller particles which fly a part with high energy. (Subsequent pulses will vaporize the smaller particles created by the earlier pulses.)

Figure 6:
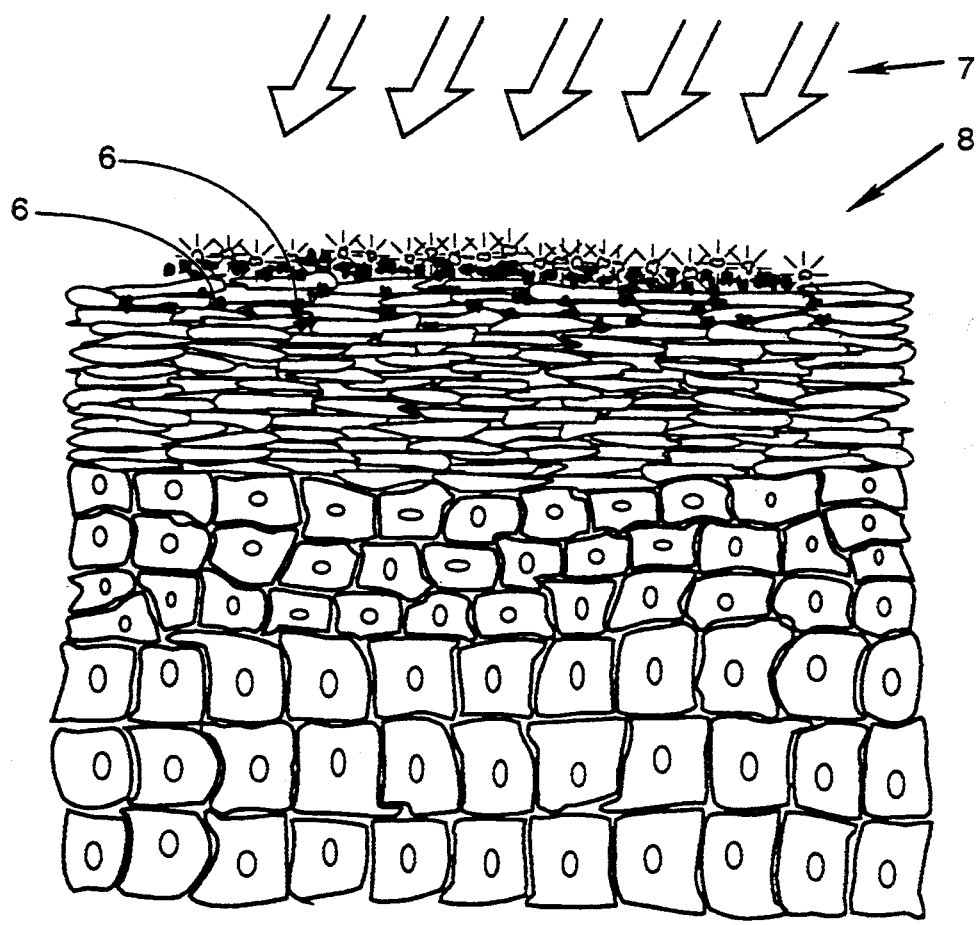
FIG. 6 shows a laser pulse exploding some particles.
Figure 7:
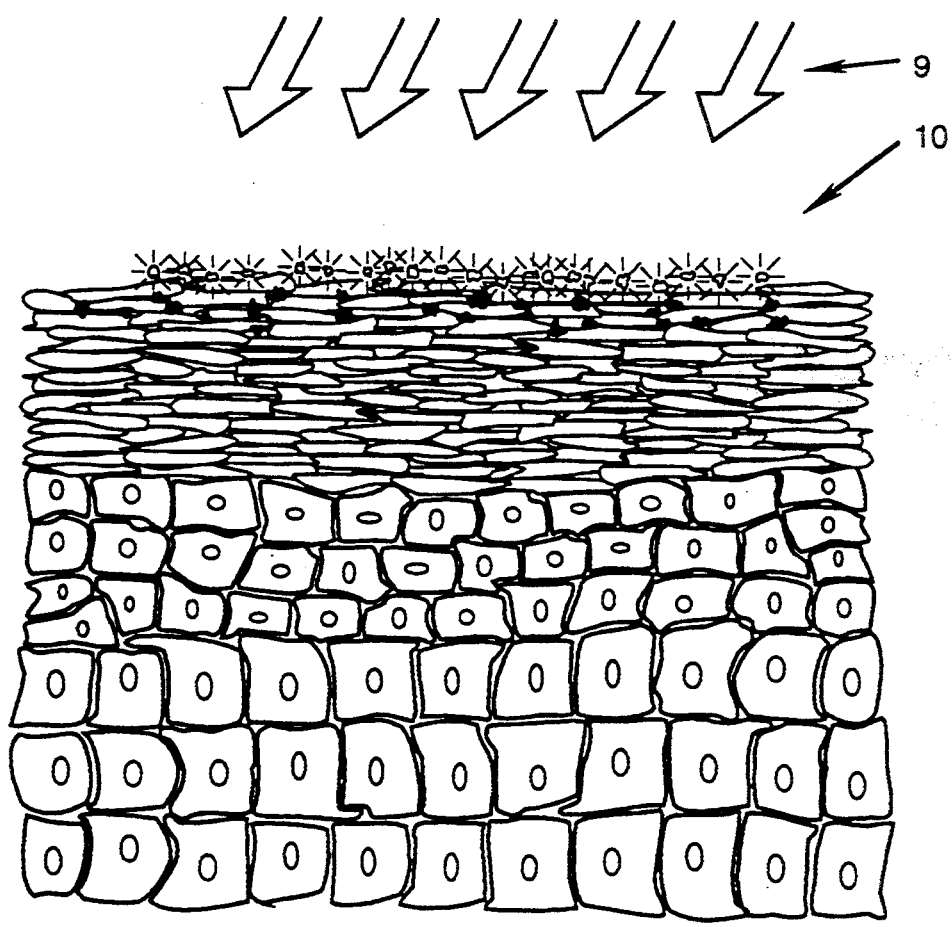
FIG. 7 shows a second laser pulse.
Figure 8:
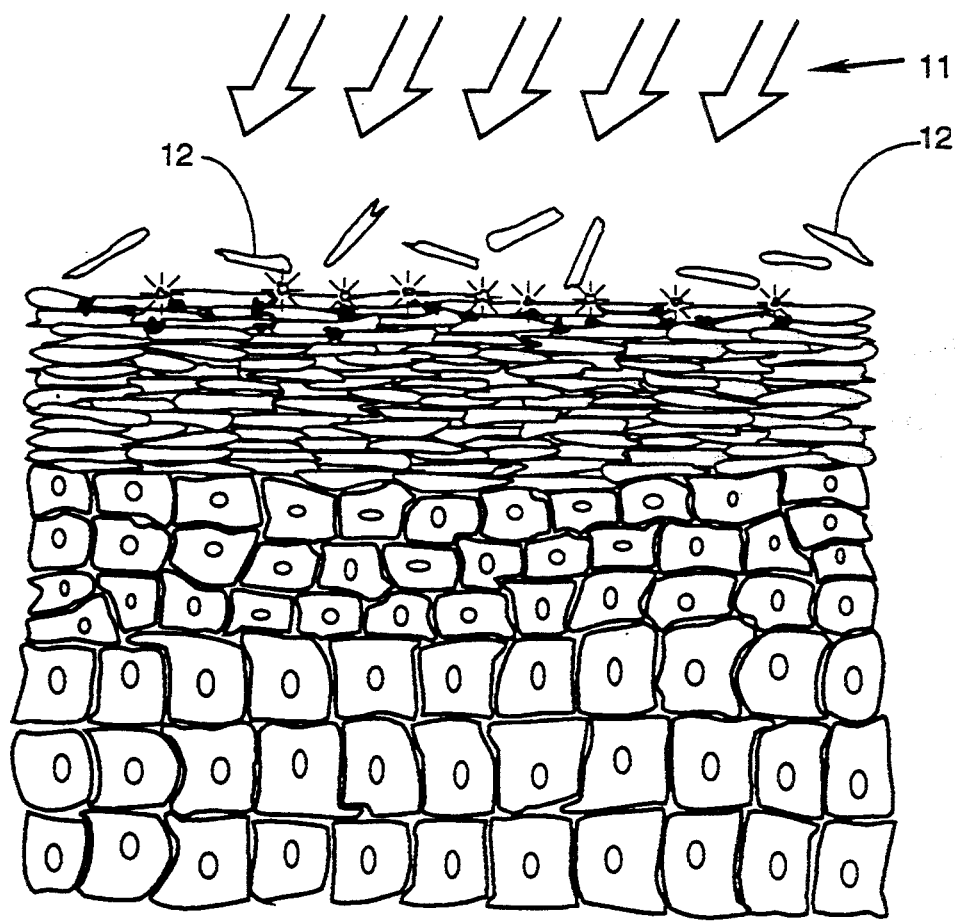
FIG. 8 shows a skin cells being torn off.
Figure 9:
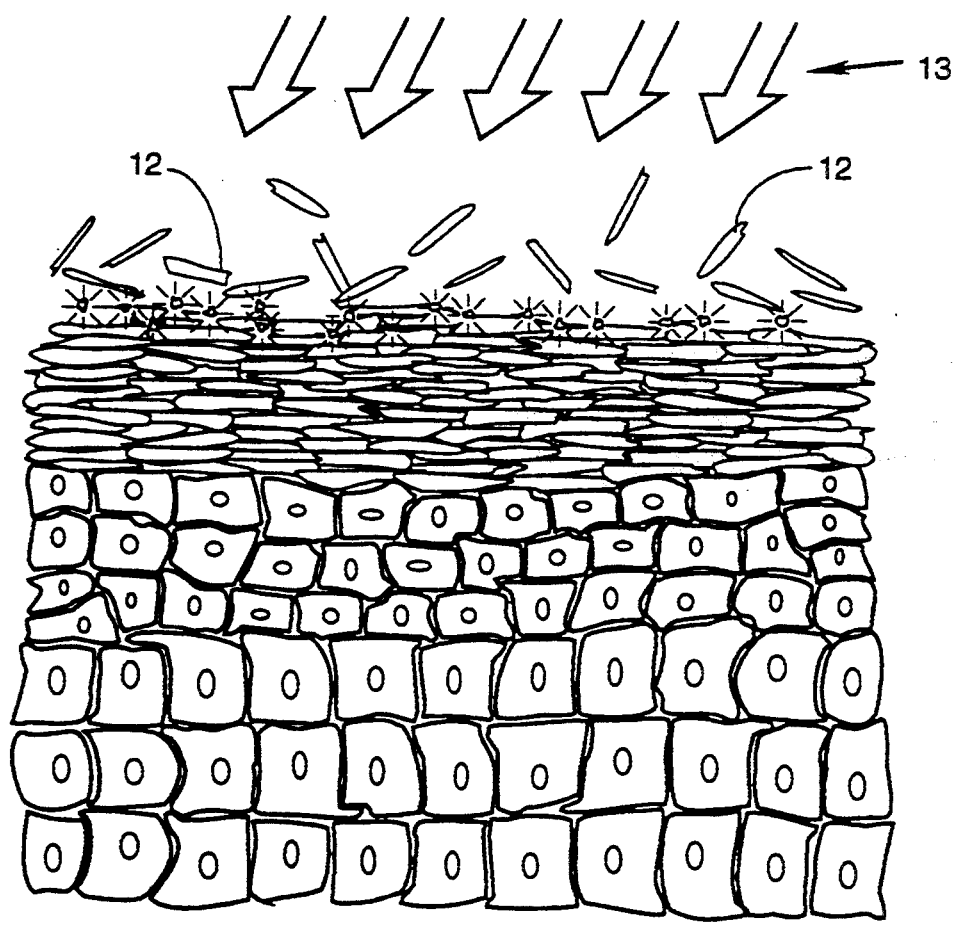
FIG. 9 shows more skin cells being torn off.

Thus, as a result of the first pulse 7 the first layer of graphite particles is exploded as shown at 8 in FIG. 6. The second layer and the skin surface is effectively shielded from the first pulse 7 by the first layer. Some of the carbon particles above the skin have been pushed into the skin as a result of the shockwaves resulting from the explosion of the particle in the first layer. The second pulse 9 coming one second later, vaporizes the second layer as shown at 10 in FIG. 7. As before, additional particles are pushed into the skin. The skin is fairly effectively shielded from pulse 9 by the second layer. But the third pulse 11 interacts with the skin and the carbon particle below the skin. Laser energy at a 1.06 wavelength has an extinction length in human skin of several cm so very little of the energy of the pulse is absorbed in the skin tissue but it is highly absorbed in the graphite particles below the surface and upon absorption of the energy from third pulse 11 as shown in FIG. 8, the particles explode violently ripping off the dead cells of the stratum corneum which lay above the exploding cells all as shown in FIG. 8. A few particles may be shielded from pulse 11 but three of four additional pulses 13 will assure that essentially all graphite particles are exploded as shown in FIG. 9.

Figure 10:
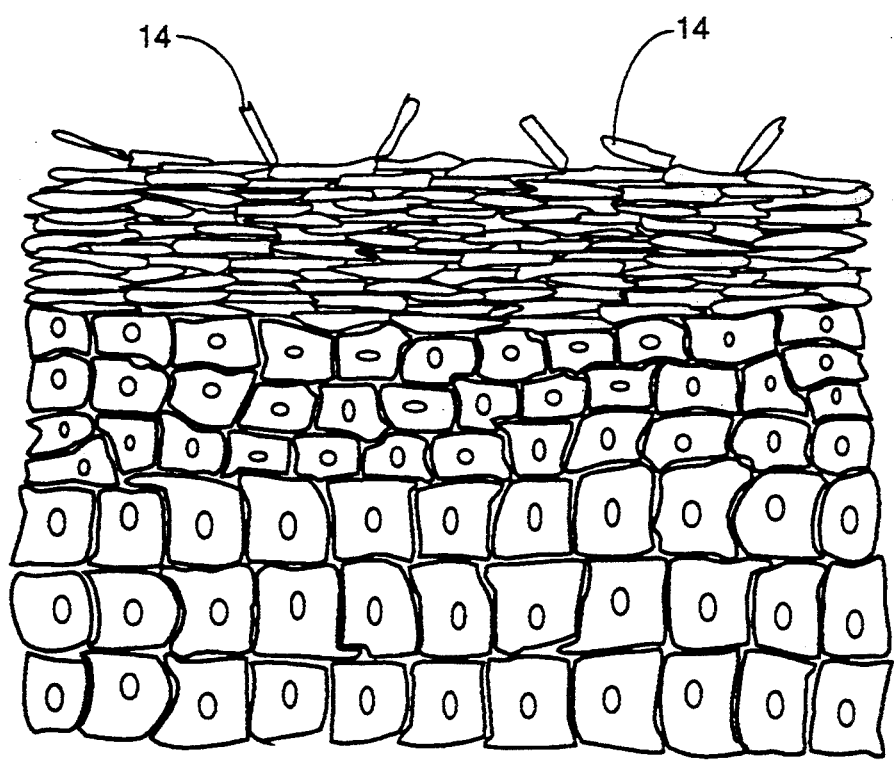
FIG. 10 shows the result of the laser pulses.
Figure 11:
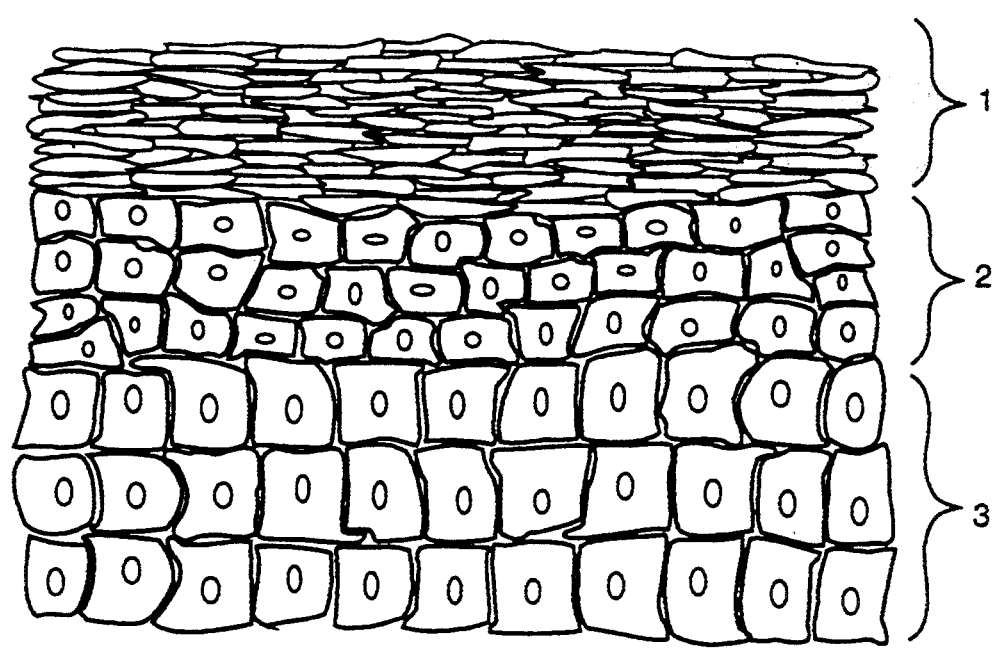
FIG. 11 shows the result of cleaning off the loose cells.

FIG. 10 shows a cross section view of the skin surface after the laser irradiation. This drawing is based on pig skin biopsy results of skin treated as described above. The skin is washed lightly with an alcohol soaked cloth and allowed to dry resulting in a surface as shown in FIG. 11. The depiction as shown in FIG. 11 can be compared with that of FIG. 2. We see that about three layers of the dead cells in the stratum corneum have been removed. There is no pain, no feeling of heat and no significant injury to the skin tissue.

The Nd:YAG laser energy which was not absorbed in the carbon is harmlessly dissipated in the skin and tissue below the skin. It is preferable to provide a slight diverging beam to assure that it spreads after it hits the skin. In our preferred embodiment the spot size at the surface is 0.5 cm (diameter) and is spreading at 10 degrees.

Second Preferred Embodiment (with Confinement)

Figure 12:
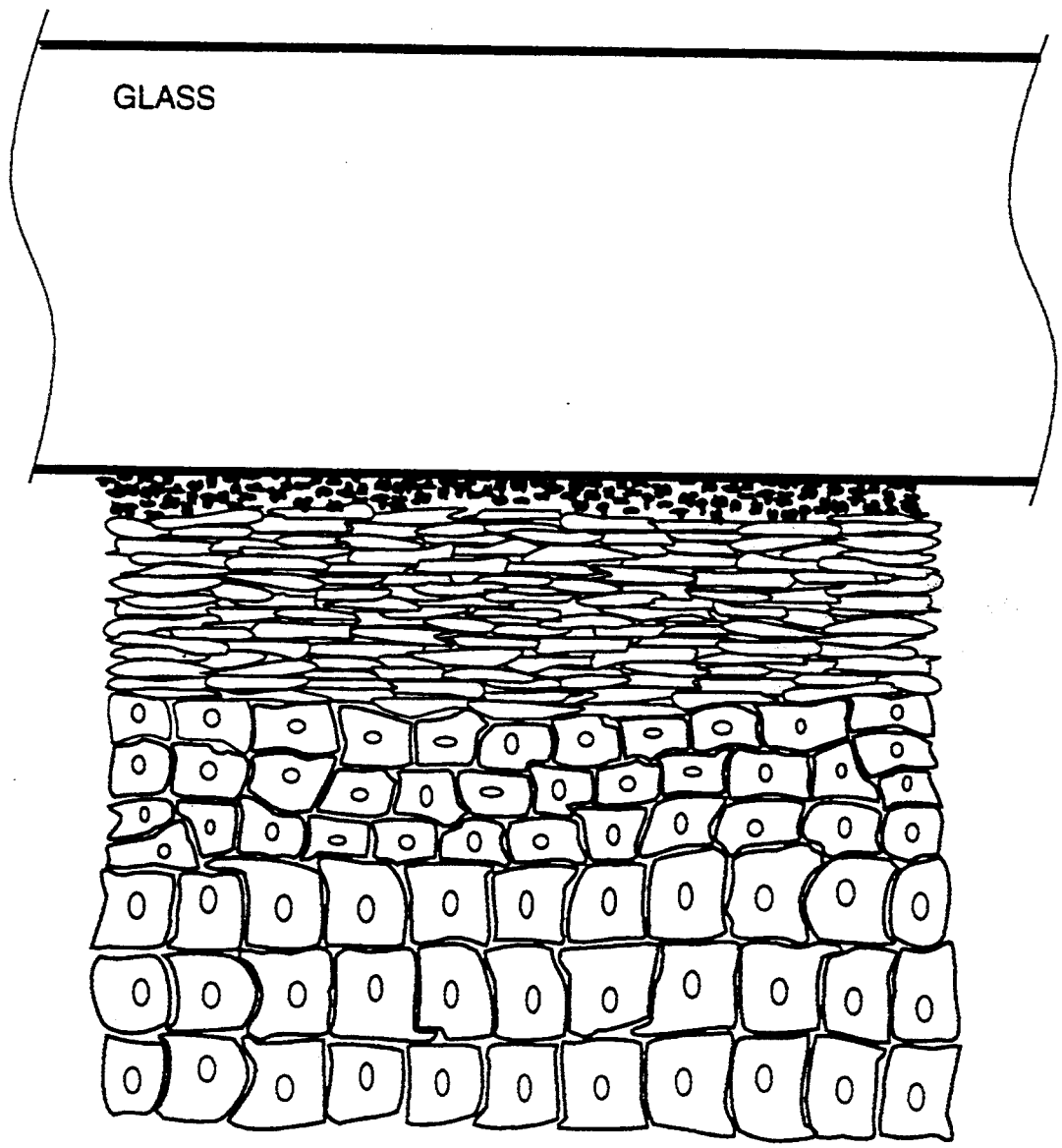
FIG. 12 shows a glass confinement plate being added.
Figure 13:
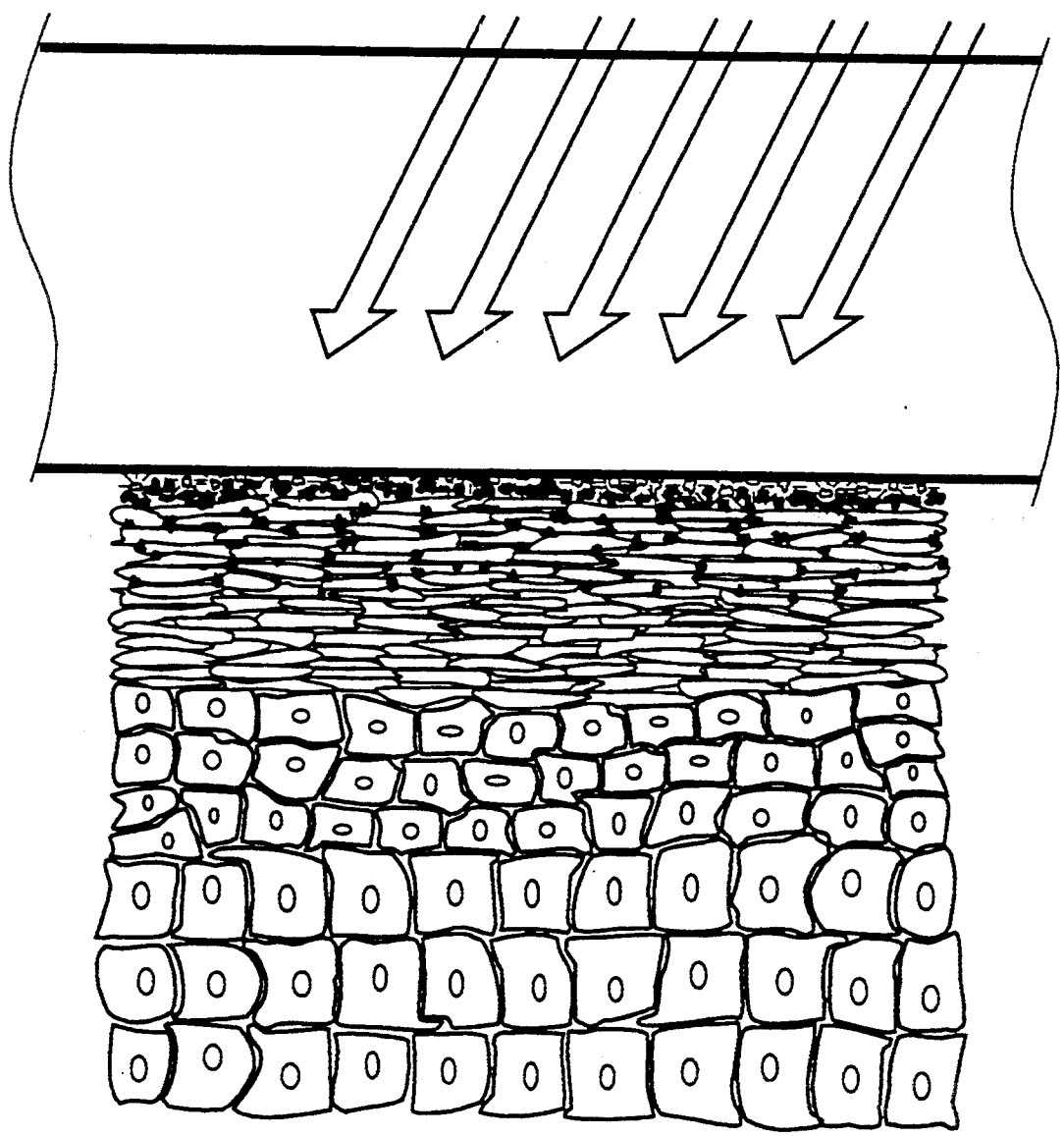
FIG. 13 shows a confined explosion under the glass.

A second preferred embodiment is the same as the first preferred embodiment except that after the carbon-oil suspension is placed on the skin surface, a thin flat piece of glass (such as a microscope glass) is placed firmly over the suspension in order to confine the small explosion and several pulses (preferably about 1 or 2) of the laser beam are applied through the glass onto each section of suspension. Also we do not use the ultrasound unit. The effect is to greatly enhance the subsurface contamination of the upper layers of the epidermis with small particles of graphite. The effect is shown in FIGS. 12 and 13. One or two pulses is sufficient to produce substantial subsurface contamination with small carbon particles. After this application the glass is removed and the process as explained above for the first embodiment is continued until essentially all of the graphite has been vaporized. In an alternate embodiment a disposable plastic plate, transparent to the laser beam could be used instead of the glass plate. The disposable plastic plate could be made a part of an articulated arm of the laser or a part of a hand piece attached to the articulated arm.

This method of forcing matter into the skin tissue can be utilized to tattoo the skin or to administer drugs through the skin. At least one of the present inventors plans to file a CIP application specifically claiming such processes.

Third Preferred Embodiment—CO$_2$

A third preferred embodiment utilizes a CO$_2$ pulse laser. Preferred operating parameters are: wavelength 10.6 micron, energy density per pulse 2.5 Joule/cm$^2$, pulse diameter 1 cm, pulse duration 50 ns. Laser beams at 10.6 micron have an extinction length in skin of about 40 micron because the pulse energy is highly absorbed in water. It is much more highly absorbed in carbon. We estimate an extinction length of 1 to 2 microns.

The process is very similar to that described above. Graphite is applied as above using the ultrasound to force some of the carbon below the surface. The laser pulses are applied as above and to the first two pulses produce similar results cleaning off the two layers of carbon. The third pulse however will in addition to vaporizing carbon below the skin surface will vaporize a thin surface of tissue. Therefore, we get the combined effect of (1) mechanical removal of tissues due to the explosion of particles below the surface and (2) vaporization of a surface layer of epidermal tissue about 2-3 microns thick.

Fourth Preferred Embodiment—Liquid Contaminant

Prepare a solution of warm water colored with black food coloring at one part color per fifty parts water. Apply to skin surface with gauze for 10 minutes. The warm black water will infiltrate into the space in the upper layers of the corneum stratum. (These spaces are normally filled with air.) Remove gauze and illuminate with about 1 or 2 pulses per site using a CO$_2$ laser operating at 10.6 microns and 50 nano second duration pulses with an energy density of 2 Joules per cm$^2$. These short pulses will deposit sufficient energy selectively to the colored water solution to vaporize instantly the water tearing off the upper most corneum stratum cells in the skin section.

An alternative to this embodiment is to add indocyanine green to the warm water instead of the black food coloring. Indocyanine green absorbs infrared light such as that produced by the Nd:YAG, $CO_2$, Alexandrite, Ti: Sapphire and Ga:As diode lasers. Since water is an excellent absorber of $CO_2$ laser energy, many water based skin lotions could be used with the $CO_2$ laser.

Other Embodiments

Persons skilled in the laser-mediucian art will recognize that many other lasers-contaminant combination could be used to practice this invention. The important attributes of the combinations are:

1) The contaminant must be very highly absorptive of energy at the wavelength of the laser beam.
2) The laser beam must be a pulsed beam with very short pulses (pulse duration of less than 1 microsecond).
3) The contaminant must be capable of being infiltrated into the upper layers of the epidermis.
4) The contaminant must explode with sufficient energy to tear off epidermis cells upon absorption of the laser energy.

Applicants have tested acrylic tattoo inks which have been approved by FDA for tattoo use. Black and blue tattoo inks marketed by Spaulding and Rogers appear to work well with a Nd:YAG laser operating at 1 Hz, 1.06 micron with an energy density of about 3 $J/cm^2$. We had less success with other colors.

While the above description contains many specifications, the reader should not construe these as limitations on the scope of the invention, by merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

We claim:

1. A process for the removal of superficial epidermal skin cells in human skin comprising the steps of:
   a. topically applying to a section of said skin a contaminant having a high absorption at at least one frequency band of light which penetrates the outer layers of human epidermis,
   b. forcing some of said contaminant to infiltrate into spaces between said superficial epidermal skins cells, and
   c. illuminating said section of skin with pulses of said at least one frequency band of light, at least one of said pulses having sufficient energy to cause at least a portion of said contaminant to explode so as to tear off some of said superficial epidermal skin cells.

2. A process as in claim 1 wherein said contaminant comprises a large number of carbon particles.

3. A process as in claim 2 wherein an ultrasound device is utilized to force said some of the carbon particles to infiltrate into said spaces.

4. A process as in claim 2 wherein said carbon particles are graphite particles.

5. A process as in claim 4 wherein said graphite particles are mixed with an oil.

6. A process as in claim 5 wherein said oil is baby oil.

7. A process as in claim 2 wherein said carbon particles have a major dimension of about 1 micron.

8. A process as in claim 2 wherein said pulses are pulses from a Nd:YAG laser.

9. A process as in claim 2 wherein said pulses are pulses from a $CO_2$ laser.

10. A process as in claim 1 wherein at least one forcing explosion of a portion of said contaminant is utilized to force said some of the contaminant to infiltrate into said spaces.

11. A process as in claim 1 wherein a confinement means, transparent to said at least one frequency band of light is placed firmly over said topically applied contaminant for the duration of said forcing explosion for the purpose of confining said forcing explosion.

12. A process as in claim 11 wherein said confinement means is a glass plate.

13. A process as in claim 11 wherein said confinement means is a plastic plate.

14. A process as in claim 13 wherein said plastic plate is a part of an articulated arm.

* * * * *